United States Patent
Modi

(10) Patent No.: US 6,315,984 B1
(45) Date of Patent: *Nov. 13, 2001

(54) PRESSURIZED CONTAINER HAVING AN AEROSOLIZED PHARMACEUTICAL COMPOSITION

(75) Inventor: Pankaj Modi, Ancaster (CA)

(73) Assignee: Generex Pharmaceuticals, Inc., Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/388,344

(22) Filed: Sep. 3, 1999

Related U.S. Application Data

(63) Continuation-in-part of application No. 09/272,563, filed on Mar. 19, 1999.

(51) Int. Cl.[7] ........................................................ A61K 9/12
(52) U.S. Cl. ........................... 424/45; 424/46; 424/450; 424/725; 424/764; 424/758; 424/85.1; 424/85.2; 424/85.4; 424/130.1; 424/184.1; 424/236.1; 514/2
(58) Field of Search ............................ 424/45, 46, 195.1, 424/450, 725, 764, 758, 85.1, 85.2, 85.4, 130.1, 184.1, 236.1; 514/2

(56) References Cited

U.S. PATENT DOCUMENTS

| | | |
|---|---|---|
| 4,579,730 | 4/1986 | Kidron et al. . |
| 4,582,820 | 4/1986 | Teng . |
| 5,006,343 | 4/1991 | Benson et al. . |
| 5,053,389 | 10/1991 | Balschmidt et al. . |
| 5,230,884 | 7/1993 | Evans et al. . |
| 5,288,497 | 2/1994 | Stanley et al. . |
| 5,306,483 * | 4/1994 | Mautone . |
| 5,653,987 | 8/1997 | Modi et al. . |
| 5,658,878 | 8/1997 | Backstrom et al. . |
| 5,665,700 | 9/1997 | Cho et al. . |
| 5,672,581 | 9/1997 | Rubsamen et al. . |
| 5,676,931 | 10/1997 | Adjei et al. . |
| 5,690,954 | 11/1997 | Illum . |
| 5,747,445 | 5/1998 | Backstrom et al. . |
| 5,853,748 | 12/1998 | New . |
| 5,898,028 | 4/1999 | Jensen et al. . |
| 5,952,008 | 9/1999 | Backstrom et al. . |
| 5,985,309 | 11/1999 | Edwards et al. . |
| 6,017,545 | 1/2000 | Modi . |
| 6,193,997 * | 2/2001 | Modi . |
| 6,214,375 * | 4/2001 | Modi . |
| 6,221,378 * | 4/2001 | Modi . |
| 6,271,200 * | 8/2001 | Modi . |

OTHER PUBLICATIONS

Kohler, D. (1993). Systemic Therapy With Aerosols. In: Aerosols in Medicine (Morén et al. eds.), Elsevier Science Publishers, pp. 303–319.*

Patton et al. (1992). Advanced Drug Delivery Reviews, vol. 8, pp. 179–196.*

* cited by examiner

*Primary Examiner*—Raj Bawa
(74) *Attorney, Agent, or Firm*—Debra Z. Anderson; Eckert Seamans Cherin & Mellott, LLC

(57) ABSTRACT

A pressurized container with an aerosol pharmaceutical formulation, and a process for making the formulation, are provided. The formulation comprises a pharmaceutical agent, a phenol, glycerin or polyglycerin, and an additional ingredient such as an alkali metal alkyl sulfate, polidocanol alkyl ether or the like. The formulation is placed in the pressurized container, which is then charged with a propellant. A method of treating a medical condition, by spraying the formulation into the mouth or lungs, is also provided.

27 Claims, No Drawings

PRESSURIZED CONTAINER HAVING AN AEROSOLIZED PHARMACEUTICAL COMPOSITION

This is a continuation-in-part of application Ser. No. 09/272,563 filed Mar. 19, 1999.

FIELD OF THE INVENTION

The present invention relates to an improved delivery system for the administration of large-molecule pharmaceuticals, e.g. peptidic drugs, vaccines and hormones. In particular it relates to pharmaceuticals which may be administered by means of an aerosol into the mouth, for buccal or pulmonary application.

BACKGROUND TO THE INVENTION

Sub-optimal disease management for respiratory illnesses, e.g. asthma, cystic fibrosis, and chronic obstructive pulmonary disease (COPD) collectively represents about 20 billion dollar worldwide market for biotechnology-derived proteins. The pulmonary delivered protein, represent an enormous market opportunity for pulmonary drug delivery. The delivery of drugs via inhalation for local delivery to the upper lung (most commonly in the form of metered-dose inhalers) and for systemic delivery (into the bloodstream) via the deep lung defines the scope of pulmonary drug delivery, is the subject of intense research.

For more than a decade, companies have searched extensively to find a drug delivery technology which is patient-friendly, non-invasive, and an economically viable alternative to injecting the large macromolecule proteins. Some of the earliest efforts involved transdermal delivery via electroporations but this has mostly been abandoned as large molecules simply can't pass through the skin. Oral delivery, which would clearly be the preferable dosage form, has had some success, but a major obstacle is the degradation and denaturization of proteins in the gastrointestinal tract.

Drug delivery through the lung appears optimal for two major reasons, i.e. the enormous surface area available for delivery, and permeability to large molecules. The lung has about a half billion alveoli. The alveoli in an average adult lung have a surface area the size of a tennis court, far exceeding the surface area of most other delivery routes, e.g. GI tract, by several orders of magnitude. The alveoli allow oxygen and other molecules to readily pass into the circulatory system. Conventional metered dose inhalers, primarily used for asthma, deliver drugs into the upper branches of the lung. In terms of permeability, the buccal cavity and lung are ideal absorption areas for both small and large molecules. Large proteins, including antibodies, are readily absorbed through the alveoli either directly into the circulatory system or, more frequently, via the lymphatic system, which subsequently releases the drug into the bloodstream.

The ability to deliver large molecule drugs orally, e.g. buccally, and/or into the deep lung will represent one of the most significant technical breakthroughs in drug delivery.

New products that address these drug delivery needs are sought, which simultaneously provide patients with a convenient user friendly mechanism and physicians with a tool to improve therapy, compliance, and to prevent or reduce expensive hospital stays.

Oral delivery offers a variety of benefits for systemic drug delivery. For example, it provides easy, non-invasive access to a permeable mucosa, which facilitates rapid drug absorption and a fast onset of action of the drug. In comparison to the GI tract and other organs, the buccal environment has lower enzymatic activity and a neutral pH.

The absorption of proteins and peptides is believed to be enhanced by the diffusion of large molecules entrapped in droplet form through the aqueous pores and the cell structure perturbation of the tight paracellular junctions. In order to further improve the penetration and absorption of formulation it has now been found that such formulations can be mixed with a propellant (preferably a non-CFC) and delivered, e.g. applied to the buccal mucosa, through metered dose inhalers (MDIs) or similar. The present invention uses novel formulations that are intended to improve the quality (in terms of absorption), stability, and performance of MDI-delivered pharmaceuticals. A novel method is used to solubilize drugs in a propellant. The formulation ingredients are selected specifically to give enhancement in the penetration through the pores and facilitate the absorption of the drugs to reach therapeutic levels in the plasma.

With previous formulations, in order to administer the pharmaceutical agent, it is necessary to shake the vial in order to temporarily intimately mix the two phases, so that a mixture of pharmaceutical formulation and propellant are expelled from the vial upon opening a dosing valve. The propellant and pharmaceutical phases quickly separate after shaking. Separation of the phases may lead to situations wherein the person administering the drug does not shake the vial sufficiently, forgets to shake the vial or waits too long before opening the dosing valve. Such situations lead to a lack of uniformity in the amount of pharmaceutical being administered from one opening of the valve to the next, i.e. from "shot" to "shot". This is particularly problematic where the amount of pharmaceutical agent to be administered is critical, e.g. with insulin and some pain killing drugs and narcotics. It is desirable, therefore, for the formulation and propellant to be evenly mixed, e.g. as a solution, stable suspension or the like.

The present invention is directed to providing a stable mixture of propellant and pharmaceutical agent.

The terms "comprising" and "comprises" when used in this specification are taken to specify the presence of the stated features, integers, steps or components but do not preclude the presence or addition of one or more other features, integers, steps, components or groups thereof.

The term "solubilized" is used in this specification to refer to a stable intimate mixture of ingredients. It has not been determined whether the mixture is a solution, suspension or other form of intimate mixture. Such a solubilized mixture is stable for substantial periods of time, e.g. months, without separation.

SUMMARY OF THE INVENTION

Accordingly the present invention provides a pressurized container containing a stable solubilized mixture of propellant which is liquid under pressure and an intermediate formulation which comprises a proteinic pharmaceutical agent, water, first ingredient, second ingredient and at least one third ingredient, wherein the first ingredient is selected from glycerin and polyglycerin and mixtures thereof in an amount of from 1–50 wt./wt. % of the intermediate formulation, the second ingredient is selected from phenol, methyl phenol and mixtures thereof in an amount of from 1–20 wt./wt. % of the intermediate formulation, each third ingredient is selected from the group consisting of alkali metal C8 to C22 alkyl sulphate, polidocanol C6 to C40 alkyl ethers, trihydroxy oxo-cholanyl glycines and pharmaceutically acceptable salts thereof, polyoxyethylene ethers, alkyl-aryl polyether alcohols, hyaluronic acid and pharmaceutically suitable salts thereof, monoolein, triolein, lysine, polylysine, oleic acid, linoleic acid, linolenic acid, monooleates and laurates, glycolic acid, lactic acid, chenodeoxycholate, deoxycholate, chamomile extract, cucumber extract, borage oil and evening of primrose oil and mixtures thereof, in an amount of from 1–50 wt./wt. % of the intermediate formulation, and wherein the total concentration of first, second and third ingredients is less than 90 wt./wt. % of the intermediate formulation.

In one embodiment, the alkali metal C8 to C22 alkyl sulphate is in a concentration of from 2 to 20 wt./wt. % of the intermediate formulation, especially 5 to 15 wt./wt. %.

In a further embodiment, the methyl phenol is m-cresol.

In another embodiment, the alkali metal C8 to C22 alkyl sulphate is sodium lauryl sulphate.

In a further embodiment the polidocanol alkyl ether is a polidocanol 10 or 20 lauryl ether.

In another embodiment, the polyoxyethylene ether is polyoxyethylene sorbitan ether, and particularly polyoxyethylene sorbitan 80 lauryl ether.

In yet another embodiment, the third ingredient is present in a concentration of from about 1 to about 25 wt./wt. %.

In yet another embodiment, the propellant is selected from the group consisting of tetrafluoroethane, tetrafluoropropane, dimethylfluoropropane, heptafluoropropane, dimethyl ether, n-butane and isobutane.

In a further embodiment, the weight ratio of intermediate formulation to propellant is from 5:95 to 25:75.

In one embodiment, the pharmaceutical agent, water, first, second and third ingredients and propellant have been solubilized by a process comprising the steps of:

a) dissolving the proteinic pharmaceutical agent in water and adjusting the pH to a level suitable for pharmaceutical use;
b) mixing with the first ingredient in an amount of from 1–50 wt./wt. % of the intermediate formulation;
c) then mixing with the second ingredient in an amount of from 1–20 wt./wt. % of the intermediate formulation;
d) subsequently adding and mixing at least one third ingredient to form the intermediate formulation;
e) charging the intermediate formulation to a pressurizable container and subsequently charging the container with the propellant.

The invention also provides a process for making a stable aerosol pharmaceutical composition in which a propellant and an intermediate formulation, which comprises a pharmaceutical agent, water and first, second and third ingredients, has been solubilized by a process comprising the steps of:

a) dissolving the proteinic pharmaceutical agent in water and adjusting the pH to a level suitable for pharmaceutical use;
b) mixing with a first ingredient selected from glycerin, polyglycerin and mixtures thereof in an amount of from 1–50 wt./wt. % of the intermediate formulation;
c) then mixing with a second ingredient selected from phenol, methyl phenol and mixtures thereof in an amount of from 1–20 wt./wt. % of the intermediate formulation;
d) subsequently adding and mixing at least one third ingredient to form the intermediate formulation, said third ingredient being selected from the group consisting of alkali metal C8 to C22 alkyl sulphate, polidocanol C6 to C40 alkyl ethers, trihydroxy oxocholanyl glycines and pharmaceutically acceptable salts thereof, polyoxyethylene ethers, alkyl-aryl polyether alcohols, hyaluronic acid and pharmaceutically suitable salts thereof, monoolein, triolein, lysine, polylysine, oleic acid, linoleic acid, linolenic acid, monooleates and laurates, glycolic acid, lactic acid, chenodeoxycholate, deoxycholate, chamomile extract, cucumber extract, borage oil and evening of primrose oil and mixtures thereof, each of said third ingredients being present in an amount of from 1–50 wt./wt. % of the intermediate formulation, and wherein the total concentration of first, second and third ingredients ate less than 90 wt./wt. % of the intermediate formulation;
e) charging the intermediate formulation to a pressurizable container and subsequently charging the container with the propellant.

In one embodiment, the alkali metal C8 to C22 alkyl sulphate is in a concentration of from 2 to 25 wt./wt. % of the intermediate formulation.

In a further embodiment, the methyl phenol is m-cresol.

In another embodiment, the alkali metal C8 to C22 alkyl sulphate is sodium lauryl sulphate.

In a further embodiment the polidocanol alkyl ether is a polidocanol 10 or 20 lauryl ether.

In another embodiment, the polyoxyethylene ether is polyoxyethylene sorbitan ether, particularly polyoxyethylene sorbitan 80 lauryl ether.

In yet another embodiment, the third ingredient is present in a concentration of from about 1 to about 25 wt./wt. %.

In another embodiment, in step a) the pH is adjusted to between 6.0 and 9.0, and preferably between 7.0. and 8.0.

In yet another embodiment, the propellant is selected from the group consisting of tetrafluoroethane, tetrafluoropropane, dimethylfluoropropane, heptafluoropropane, dimethyl ether, n-butane and isobutane.

In a further embodiment, the weight ratio of intermediate formulation to propellant is from 5:95 to 25:75.

In yet another embodiment, step d) is accomplished with a high speed mixer or sonicator.

The present invention also provides a metered dose aerosol dispenser with the stable aerosol pharmaceutical composition of the present invention therein.

The present invention also provides a method for administering stable aerosol pharmaceutical compositions of the present invention, by spraying a predetermined amount of the composition into the mouth with a metered dose spray device.

The present invention also provides a method for administration of a proteinic pharmaceutical agent in a buccal cavity of a human being by spraying into the cavity, without inhalation, from a metered dose spray dispenser, a predetermined amount of stable solubilized mixture of propellant which is liquid under pressure and an intermediate formulation which comprises a proteinic pharmaceutical agent, water, first ingredient, second ingredient and. at least one third ingredient, wherein the first ingredient is selected from glycerin and polyglycerin and mixtures thereof in an amount of from 1–50 wt./wt. % of the intermediate formulation, the second ingredient is selected from phenol, methyl phenol and mixtures thereof in an amount of from 1–20 wt./wt. % of the intermediate formulation, each third ingredient is selected from the group consisting of alkali metal C8 to C22 alkyl sulphate, polidocanol C6 to C40 alkyl ethers, trihydroxy oxo-cholanyl glycines and pharmaceutically acceptable salts thereof, polyoxyethylene ethers, alkyl-aryl polyether alcohols, hyaluronic acid and pharmaceutically suitable salts thereof, monoolein, triolein, lysine, polylysine, oleic acid, linoleic acid, linolenic acid, monooleates and laurates, glycolic acid, lactic acid, chenodeoxycholate, deoxycholate, chamomile extract, cucumber extract, borage oil and evening of primrose oil and mixtures thereof, in an amount of from 1–50 wt./wt. % of the intermediate formulation, and wherein the total concentration of first, second and third ingredients is less than 90 wt./wt. % of the intermediate formulation.

DETAILED DESCRIPTION OF PREFERRED EMBODIMENTS

The present invention provides an improved, stable formulation. The formulation allows delivery of macromolecular (high molecular weight) pharmaceutical agents, particularly through the membranes in the mouth or lungs.

The pharmaceutical agents cover a wide spectrum of agents, including proteins, peptides, hormones, vaccines and drugs. The molecular weights of the macromolecular pharmaceutical agents are preferably above 1000, especially between 1000 and 2 000 000.

The proteinic pharmaceutical agent may be selected from a wide variety of macromolecular agents, depending on the disorder being treated, generally with molecular weights greater than about 1000 and especially between about 1000 and 2 000 000. Preferred pharmaceutical agents are selected from the group consisting of insulin, heparin, low molecular weight heparin, hirulog, hirugen, huridine, interferons, interleukins, cytokins, mono and polyclonal antibodies, immunoglobins, chemotherapeutic agents, vaccines, glycoproteins, bacterial toxoids, hormones, calcitonins, insulin like growth factors (IGF), glucagon like peptides (GLP-1), large molecule antibiotics, protein based thrombolytic compounds, platelet inhibitors, DNA, RNA, gene therapeutics and antisense oligonucleotides and many injectable opiods, narcotics, hypnotics, steroids and pain killers (non-steroidal anti-inflammatory drugs).

As will be understood, the concentration of the pharmaceutical agent is an amount sufficient to be effective in treating or preventing a disorder or to regulate a physiological condition in an animal or human. The concentration or amount of pharmaceutical agent administered will depend on the parameters determined for the agent and the method of administration, e.g. nasal, buccal, pulmonary. For example, nasal formulations tend to require much lower concentrations of some ingredients in order to avoid irritation or burning of the nasal passages. It is sometimes desirable to dilute an oral formulation up to 10–100 times in order to provide a suitable nasal formulation.

For insulin-containing and some other compositions, the composition may also contains at least one inorganic salt which helps to open channels in the membranes of the mouth or lungs, and may provide additional stimulation to release insulin. Non-limiting examples of inorganic salts are sodium, potassium, calcium and zinc salts, especially sodium chloride, potassium chloride, calcium chloride, zinc chloride and sodium bicarbonate.

It will be recognized by those skilled in the art that for many pharmaceutical compositions it is usual to add at least one antioxidant to prevent degradation and oxidation of the pharmaceutically active ingredients. It will also be understood by those skilled in the art that colorants, flavouring agents and non-therapeutic amounts of other compounds may be included in the formulation. Typical flavouring agents are menthol, sorbitol and fruit flavours.

The antioxidant may be selected from the group consisting of tocopherol, deteroxime mesylate, methyl araben, ethyl paraben and ascorbic acid and mixtures thereof. A preferred antioxidant is tocopherol.

In a preferred embodiment at least one protease inhibitor is added to the formulation to inhibit degradation of the pharmaceutical agent by the action of proteolytic enzymes. Of the known protease inhibitors, most are effective at concentrations of from 1 to 3 wt./wt. % of the formulation.

Non-limiting examples of effective protease inhibitors are bacitracin, soyabean trypsin, aprotinin and bacitracin derivatives, e.g. bacitracin methylene disalicylate. Bacitracin is the most effective of those named when used in concentrations of from 1.5 to 2 wt./wt. %. Soyabean trypsin and aprotinin two may be used in concentrations of about 1 to 2 wt./wt. % of the formulation.

The amount of the first ingredient is present in a concentration of from 1 to 50 wt/wt % of the intermediate formulation. The amount of the second ingredient is present in a concentration of from 1 to 20 wt/wt % of the intermediate formulation and the third ingredient is present in a concentration of from 1 to 50 wt./wt % of the intermediate formulation, and total concentration of such ingredients is less than 90 wt./wt % of the formulation. It is believed that the phenolic compounds act mainly as preservatives and complexing agents to stabilize drugs, e.g. insulin. Besides their function as a stabilizer and preservative, they may also act as antiseptic agents and furthermore may help in absorption. The methyl phenol may be o-cresol, m-cresol or p-cresol, but m-cresol is preferred.

The order of addition of the ingredients in the formulation are important in order to obtain a stable mixture. First, the pharmaceutical agent is dissolved in water. Preferably, the pH is adjusted to between about 6.0 and 9.0, and even more preferably to between about 7.0 and 8.0. Secondly, the aqueous pharmaceutical agent mixture is mixed first with glycerin, polyglycerin or mixtures thereof (the first ingredient), and then with phenol, methyl phenol or mixtures thereof (the second ingredient). Subsequently the third ingredient is added and mixed to form the intermediate formulation. The third ingredient is at least one of the following compounds: alkali metal C8 to C22 alkyl sulphate, polidocanol C6 to C40 alkyl ethers, trihydroxy oxo-cholanyl glycines and pharmaceutically acceptable salts thereof, polyoxyethylene ethers, alkyl-aryl polyether alcohols, hyaluronic acid and pharmaceutically suitable salts thereof, monoolein, triolein, lysine, polylysine, oleic acid, linoleic acid, linolenic acid, monooleates and laurates, glycolic acid, lactic acid, chenodeoxycholate, deoxycholate, chamomile extract, cucumber extract, borage oil and evening of primrose oil. The ingredients are mixed together with a mixer. When the third ingredient is added, a high speed mixer or sonicator is preferred. The resulting mixture is referred to herein as the intermediate formulation.

Each of the non-pharmaceutical substances referred to in the previous paragraph may be added in concentrations previously indicated, provided that the total amount of such substances does not exceed 90 wt./wt. % of the intermediate formulation.

After formation of the intermediate formulation, the formulation is charged to a pressurizable container. Preferably the container is a vial suitable for use with a metered dose inhaler-or applicator. Then the vial is charged with propellant. As the propellant is introduced into the vial, there is great turbulence in the vial and the propellant and pharmaceutical formulation become intimately mixed and do not separate on standing. It is believed that the propellant and pharmaceutical mixture so formed would be stable for several months. As a result, it is not necessary to shake the vial before use, although, through habit with other formulations, many users may shake the vial. The advantage of the solubilized formulation will be immediately apparent to those skilled in the art. For example, the relative homogeneity of the mixture provides good accuracy of pharmaceutical dispensing from "shot" to "shot" and from the first shot to the last from the container. As is known, in order to deliver the pharmaceutical agent to the lung, it is necessary for the user to breathe deeply when the aerosol spray from the pressurized container is released. Without breathing in, the pharmaceutical agent is delivered to the buccal cavity. The method chosen will depend on a number of factors, including the type of pharmaceutical agent, the concentration in the aerosol, the desired rate of absorption required and the like.

A particular advantage with the use of metered dose applicators or inhalers is that the formulation can be delivered in a relatively precise dose, e.g. titratable to injection within 1 unit of insulin dose. The droplet size of the formulation preferably falls between 1–5 $\mu$m in order for droplets to penetrate buccal mucosa or to reach to the deep lung surface. Thus, the present invention is suitable for delivery of proteinic drugs such as insulin for the treatment of diabetes.

The pressurized inhalers also offer a wide dosing range and consistent dosing efficiency. With such a delivery, greater than about 95% of the dose may reach the target area. The smaller particle size (1–5 $\mu$m) obtained using pressurized inhalers also enhances dosing due to broader coverage within the lung cavity. In this situation, increased coverage can help more absorption of a drug like insulin. Furthermore, because these devices are self-contained, potential contamination is avoided.

The amount of physiologically peptide or protein in the compositions of this invention is typically a quantity that provides an effective amount of the drug to produce the physiological activity (therapeutic plasma level) for which peptide or protein is being administered. In consideration of the fact that the bioavailability of any active substance can never be 100%, that is to say the administered dose of the active drug is not completely absorbed, it is preferable to incorporate slightly larger amount than the desired dosage. Where the dosage form is a spray (aerosol) or the like which is repeatedly dispensed from the same container, it is preferably so arranged that the unit dose will be slightly greater than the desired dose. It should be understood that dosage will vary with species of warm blooded animals such as man, domestic animals, and their body weights. The utilization of atomizer or aerosol spray devices (metered dose inhalers or nebulizers) is important to provide particle sizes for effective absorption from the nasal or lung cavity, or in the mouth, e.g. in the buccal cavity, so the drug may successfully absorbed or reach to the specific site. It is believed that a variety of proteins retain their biological activity even after prolonged exposure to propellants commonly used in metered dose inhalers.

The specific concentrations of the essential ingredients can be determined by relatively straightforward experimentation. It will be understood that the amounts of certain ingredients may need to be limited in order to avoid compositions which produce foam when sprayed rather than forming a fine spray. For absorption through the oral cavities, it is often desirable to increase, e.g. double or triple, the dosage which is normally required through injection or administration through the gastrointestinal tract.

As will be understood, the amount of each component of the formulation will vary depending on the pharmaceutical agent and the site of application.

The therapeutic compositions of the present invention may be stored at room temperature or at cold Adtemperature. Storage of proteinic drugs is preferable at a cold temperature to prevent degradation of the drugs and to extend their shelf life.

The desired size of aerosol droplets which are sprayed from the aerosol dispenser will depend, in part, on where the pharmaceutical is to be deposited. For example, for deposition in the lungs, particle sizes of less than about 5 $\mu$m are preferred whereas for absorption in the buccal cavity of the mouth, particle sizes of about 6–10 $\mu$m are preferred.

The amount of physiologically peptide or protein in the compositions of this invention is typically a quantity that provides an effective amount of the pharmaceutical or drug to produce the physiological activity (therapeutic plasma level) for which peptide or protein is being administered. In consideration of the fact that the bioavailability of any active substance can never be 100%, that is to say the administered dose of the active drug is not completely absorbed, it is preferable to incorporate slightly larger amount than the desired dosage.

Administration of the formulation into the buccal cavity is by spraying the formulation into the mouth, substantially without inhalation, so that the droplets stay in the mouth rather than be drawn into the lungs.

The advantages of the present invention are illustrated by the following non-limiting examples in which insulin is the pharmaceutical agent.

EXAMPLE 1

Method of Insulin Solution Preparation: (U200, 400, 600, 800 and 1000 per mL)

Appropriate quantities of insulin powder (in order to make 200 units, 400 units or 600 units 800 units or 1000 units per mL, depending on the activity (27.5–28.3 units/mg) were weighed accurately on an analytical balance. The powders were transferred to glass beakers equipped with stirrer. Distilled water was added to the beakers and the solution was stirred at low speed. To each beaker was added 5M HCl (pH 2) solution dropwise until the insulin powder therein was solubilized completely. These solutions were then neutralized with 5M NaOH dropwise to pH 7–8. The solution was stirred continuously at low speed. The solution was stirred further for 30 minutes and stored at 10° C. or at room temperature. This gave solutions containing insulin with 200U, 400U, 600U, 800U and 1000U/mL.

Glycerin was added to each of these solutions, with stirring, in an amount of 20 wt./wt. % glycerin in the intermediate formulation. After this, phenol was added, with stirring, in an amount of 10 wt./wt. % phenol in the intermediate formulation. Then 15 wt./wt % sodium lauryl sulphate, 10 wt./wt. % trihydroxy oxo cholanyl glycine and 20 wt./wt. % polidocanol 20 lauryl ether was added and mixed with a high speed stirrer.

One millilitre portions of the solutions of insulin (U200, U400, U600, U800 or U1000/mL) were pipetted into special glass vials coated on the outside with a plastic coating, for protection in the event of mechanical failure of the glass. The vials were then charged with a non-CFC tetrafluoroethane (134a) propellant with the aid of a Pamasol 2008 (trade mark) semi-automatic gas filling equipment. The amount of 134a propellant in each vial was adjusted to 9 mL shot size in order to deliver amounts of insulin equivalent to 2, 4, 6, 8 or 10 units/actuation when actuated through the valve of the vial. For example, the shot size of 2 units per actuation refers to the U200 insulin solution in a vial. The valves were specially designed to deliver exactly 100 $\mu$L spray per actuation.

Aerodynamic Particle Size: The aerodynamic particle sizes of formulations sprayed from the vials were then determined by 8-stage USP Anderson Multistage Cascade Impactor-Mark-II (trade mark). The Multistage Cascade Impactor was cleaned with methanol and air-dried at 30° C. Glass fibre filters were placed on the collection plates. Seals were aligned properly and the actuator was attached to a mouthpiece and assembled onto the USP induction port and jet stages. A vacuum pump was connected and air flow rate is set to 28.3 litres/min. Each vial was actuated twice to waste. The shots were then delivered by discharging the actuator into the mouthpiece and repeated for 25 times. The deposited insulin was collected by rinsing the mouthpiece with 0.6 mg/mL EDTA in 10 mL water at pH 8.7. The filters were carefully removed and placed in scintillation vials and the vials sonicated for 15 minutes. The quantity of the insulin was then analysed using RP-HPLC. The results are shown in Tables I, II and III for U400, U600 and U800 solutions.

TABLE I (U400, 4 units/actuation)

| Stage vol. # | mL | mg | units | units/ actuation | Actuation | Particle size μm |
|---|---|---|---|---|---|---|
| 0 | 10 | | | | | |
| 1 | 10 | | | | | |
| 2 | 10 | | | | | |
| 3 | 10 | 0.77 | 20.1 | 5 | 4.0 | 4.0 |
| 4 | 10 | 0.78 | 20.1 | 5 | 4.0 | 3.8 |
| 5 | 10 | 0.81 | 20.0 | 5 | 4.0 | 3.0 |
| 6 | 10 | 0.80 | 20.3 | 5 | 4.0 | 2.1 |
| 7 | 10 | 0.80 | 20.1 | 5 | 4.0 | 1.0 |
| 8 | 10 | 0.79 | 20.1 | 5 | 4.0 | 0.7 |

TABLE II (U600, 6 units/actuation)

| Stage vol. # | mL | mg | units | units/ actuation | Actuation | Particle size μm |
|---|---|---|---|---|---|---|
| 0 | 10 | n/d | | | | |
| 1 | 10 | n/d | | | | |
| 2 | 10 | n/d | | | | |
| 3 | 10 | 0.77 | 30.1 | 5 | 6.0 | 4.0 |
| 4 | 10 | 0.78 | 30.1 | 5 | 6.0 | 3.8 |
| 5 | 10 | 0.81 | 30.0 | 5 | 6.0 | 3.0 |
| 6 | 10 | 0.80 | 30.3 | 5 | 6.0 | 2.1 |
| 7 | 10 | 0.80 | 30.1 | 5 | 6.0 | 1.0 |
| 8 | 10 | 0.79 | 30.1 | 5 | 6.0 | 0.7 |

TABLE III (U800, 8 units/actuation)

| Stage vol. # | mL | mg | units | units/ actuation | Actuation | Particle size μm |
|---|---|---|---|---|---|---|
| 0 | 10 | n/d | | | | |
| 1 | 10 | n/d | | | | |
| 2 | 10 | n/d | | | | |
| 3 | 10 | 0.77 | 40.1 | 5 | 8.0 | 3.8 |
| 4 | 10 | 0.78 | 40.1 | 5 | 8.0 | 3.3 |
| 5 | 10 | 0.81 | 40.0 | 5 | 8.0 | 3.0 |
| 6 | 10 | 0.80 | 40.3 | 5 | 8.0 | 2.0 |

TABLE III-continued (U800, 8 units/actuation)

| Stage vol. # | mL | mg | units | units/ actuation | Actuation | Particle size μm |
|---|---|---|---|---|---|---|
| 7 | 10 | 0.80 | 40.1 | 5 | 8.0 | 1.0 |
| 8 | 10 | 0.79 | 40.1 | 5 | 8.0 | 0.6 |

Conclusion: The particle sizes were determined to be around 3 μm and stages 0–2 showed no insulin deposition indicating that most particles were smaller than 6 μm. Thus, this analysis suggests a strong likelihood of deep lung deposition, as the droplet sizes were generally smaller than 4 μm.

Shot size accuracy: The shot size accuracy was determined by firing shots in specially designed glass thiel tubes and weighing the tubes before and after the sample collection. Each vial had a capacity of 100 shots. The number of units per actuation are shown in Table IV.

TABLE IV (U400)

| | Shot Weight (g) | | |
|---|---|---|---|
| Shot Number | 4 units/act. | 6 units/act | 8 units/act |
| 10 | 0.076 | 0.090 | 0.179 |
| 15 | 0.073 | 0.093 | 0.180 |
| 20 | 0.076 | 0.096 | — |
| 25 | 0.074 | 0.094 | — |
| 30 | 0.070 | 0.090 | 0.178 |
| 40 | — | — | 0.176 |
| 70 | — | — | 0.177 |

Conclusion: The analysis indicates the uniformity of the shot size delivered through the valves. Insulin dose: The volume of insulin dose delivered, in terms of units/actuation was then determined by HPLC analysis.

The vials were actuated twice to waste. Shots were delivered by discharging the actuator into the mouthpiece and repeated for 25 times. The deposited insulin was collected by rinsing the mouthpiece with 0.6mg/mL EDTA in 10 mL water at pH 8.7, carefully remove the filters and place them in scintillation vials and sonicate the vials for 15 minutes. The quantity of the insulin was then analysed using RP-HPLC. The results for 6 and 8 units/actuation formulations are shown in Tables V and VI. Each vial had a capacity of 100 shots. Shot numbers 5–10 were at the beginning of the vial's discharge, 45–50 were in the middle and 85–90 were at the end.

TABLE V (6 units/actuation)

| Shot Nos. | Dose delivered μg | Dose delivered units |
|---|---|---|
| 5–10 | 118 | 6.2 |
| 45–50 | 110 | 6.0 |
| 85–90 | 105 | 5.8 |

TABLE VI

(8 units/actuation)

| Shot Nos. | Dose delivered μg | Dose delivered units |
|---|---|---|
| 5–10 | 173.3 | 8.1 |
| 45–50 | 171.1 | 7.9 |
| 85–90 | 172.7 | 8.0 |

Conclusion: The analysis indicates the uniformity of the dose delivered per actuation through the valves.

Clinical Results: 15 healthy volunteers were given the following doses of insulin for three days.

Day-1: 5 puffs of 4 units each (total 20 units)
Day-2: 5 puffs of 6 units each (total 30 units)
Day-1: 5 puffs of 8 units each (total 40 units)

Plasma insulin levels, in pmol/L, were measured every 15 minutes for first 90 minutes and then every 30 minutes for 2 hours. The results are shown in Table VII on the following page.

TABLE VII

| Time | Day-1 20 units | Day-2 30 units | Day-3 40 units |
|---|---|---|---|
| 0 | 35 | 38 | 42 |
| 15 | 56 | 62 | 72 |
| 30 | 89 | 97 | 112 |
| 45 | 119 | 138 | 178 |
| 60 | 160 | 178 | 202 |
| 75 | 160 | 175 | 190 |
| 90 | 142 | 157 | 173 |
| 120 | 78 | 112 | 141 |
| 150 | 62 | 87 | 92 |
| 180 | 37 | 49 | 67 |

These data shows significant absorption of insulin through buccal mucosa, oropharynx, and lungs regions.

EXAMPLE 2

As a comparison, i.e. outside the scope of the invention, tests were conducted with an insulin formulation which did not have any of the solubilizing ingredients.

Appropriate quantities of insulin powder (in order to make 200 units, 400 units or 600 units 800 units or 1000 units per mL, depending on the activity (27.5–28.3 units/mg) was weighed accurately on an analytical balance. The powders were transferred to glass beakers equipped with stirrers. Distilled water was added and the solution was stirred at low speed. To this was added 5M HCl (pH 2) solution dropwise till insulin powder was solubilized completely. This solution was then neutralized with 5M NaOH dropwise to pH 7–8. The solution was stirred continuously at low speed. The solution was stirred further for 30 minutes and stored at 10° C. This gave solutions containing insulin (200U, 400U, 600U, 800U or 1000U/mL).

Shot Size: Shot size accuracy was determined by firing shots in thiel tubes and weighing the tubes before and after the sample collection. Each vial had a capacity of 100 shots. The average shot weights for 5 sequential shots were determined, as shown in Tables VIII, IX and

TABLE VIII

(400U/mL)

| Shot # | # of Shots | Shot Weight (g) |
|---|---|---|
| 10–15 | 5 | 0.065 |
| 20–25 | 5 | 0.087 |
| 30–35 | 5 | 0.077 |
| 40–45 | 5 | 0.063 |
| 70–75 | 5 | 0.051 |

TABLE IX

(600U/mL)

| Shot # | # of Shots | Shot Weight (g) |
|---|---|---|
| 10–15 | 5 | 0.077 |
| 20–25 | 5 | 0.064 |
| 30–35 | 5 | 0.091 |
| 40–45 | 5 | 0.051 |
| 70–75 | 5 | 0.083 |

TABLE X

(800U/mL)

| Shot # | # of Shots | Shot Weight (g) |
|---|---|---|
| 10–15 | 5 | 0.049 |
| 20–25 | 5 | 0.071 |
| 30–35 | 5 | 0.065 |
| 40–45 | 5 | 0.088 |
| 70–75 | 5 | 0.102 |

Highly irregular shot weight distribution was observed due to the insolubility of insulin in the propellant and the inability to facilitate formation of small droplets Aerodynamic particle size: The aerodynamic particle sizes of formulations sprayed from the vials were determined by 8-stage USP Anderson Multistage Cascade Impactor-Mark-II (trade mark) by the same procedure outlined in Example 1. The results are shown in Tables XI and XII.

TABLE XI

| (U600, 6 units/actuation) | | | | | | |
|---|---|---|---|---|---|---|
| Stage vol. | | | | | units/ | Particle size |
| # | mL | mg | units | actuation | Actuation | μm |
| 0 | 10 | 0.91 | 56.5 | 5 | 11.3 | >9 |
| 1 | 10 | 0.60 | 46.7 | 5 | 9.3 | >7 |
| 2 | 10 | 0.42 | 33.3 | 5 | 6.7 | >5 |
| 3 | 10 | not detected | | | | |

TABLE XII (U800, 8 units/actuation)

| # | Stage vol. mL | mg | units | actuation | units/Actuation | Particle size μm |
|---|---|---|---|---|---|---|
| 0 | 10 | 0.97 | 77.7 | 5 | 15.5 | >9 |
| 1 | 10 | 0.88 | 66.9 | 5 | 13.4 | >7 |
| 2 | 10 | 0.42 | 55.6 | 5 | 11.1 | >5 |
| 3 | 10 | | | not detected | | |

This demonstrates highly irregular droplet sizes and number of units delivered through the aerosol valves.

EXAMPLE 3

Another experiment was conducted to provide data for comparative purposes. This example does not fall within the scope of the present invention.

Powdered insulin was placed in a glass beaker equipped with a stirrer. Distilled water was added and the solution was stirred at low speed. To this solution was added 5M HCl (pH 2) solution dropwise until the insulin was solubilized completely. This solution was then neutralized with 5M NaOH solution dropwise until the pH was between 7 and 8. Seven mg phenol and 7 mg m-cresol were added to the solution and mixed thoroughly. The solution was diluted with distilled water until there were 200 units insulin per millilitre of solution. One millilitre portions were then transferred to glass vials, which were then charged with 10.8 g HFA 134a propellant using a Pamasol (trade mark) 2008 semi-automatic gas filling apparatus.

The propellant and insulin solution remained as separate phases.

EXAMPLE 4

A further comparative experiment was conducted. Powdered insulin was placed in a glass beaker equipped with a stirrer. Distilled water was added and the solution was stirred at low speed. To this solution was added 5M HCl (pH 2) solution dropwise until the insulin was solubilized completely. This solution was then neutralized, while stirring slowly, with 5M NaOH solution dropwise until the pH was between 7 and 8. To this solution was added 7 mg sodium lauryl sulphate, 7 mg polyoxyethylene ether (10 lauryl) and 7 mg trihydroxy oxo cholanyl glycine and dissolved completely. Seven mg lecithin, solubilized in a water alcohol solution (7 mg/mL) was then added while stirring at high speed, i.e. 2000 rpm. The solution was stirred for 30 minutes and then stored at 10° C. The resulting mixed micellar solution had about 200 units insulin. To this mixture 5 mg phenol, 5 mg m-cresol and 10 mg glycerin were added.

The solution was pipetted (lmL/vial) into 10 mL capacity glass vials. The vials were then charged with HFA 134a propellant with a Pamasol 2008 automatic gas filling apparatus. The amount of propellant was adjusted to 9 mL shot size in order to deliver 2 units insulin per actuation of the aerosol vial. The valves of the vials were designed to deliver 100 AL spray per actuation, containing 2 units insulin. The aqueous pharmaceutical composition and the propellant remained as separate phases. Prior to discharging shots of the formulation, shaking of the vial was necessary in order to entrain the pharmaceutical in the propellant phase. After discharging a shot, the propellant separated from the aqueous pharmaceutical composition within about 20 seconds.

The aerodynamic particle size was determined by an 8-stage USP Anderson (trade mark) Cascade Impactor Mark II. The impactor was cleaned with methanol and air dried at 30° C. Glass fibre filters were placed on the collection plates. The actuator was attached to the mouthpiece of the impactor and assembled onto the USP induction port and jet stages. A vacuum pump was connected and the air flow rate set to 28.3 litres per minute. The vial was primed by shaking for 10 seconds and actuating twice to waste. The shot was delivered by discharging the actuator into the mouthpiece and repeating 25 times. The deposited insulin was collected by rinsing the mouthpiece with 0.6 mL EDTA in 10 mL water at pH 8.7. The filters were removed and placed in scintillation vials and sonicated for 15 minutes. The quantity of insulin was then analysed using RP-HPLC. The results are shown in Table XIII (2 units per actuation) and XIV (4 units per actuation).

TABLE XIII

| Stage No. | 0 | 1 | 2 | 3 |
|---|---|---|---|---|
| Volume (mL) | 10 | 10 | 10 | 10 |
| Mass (mg) | 0.79 | 0.81 | 0.78 | * |
| Units | 10.4 | 10.0 | 10.0 | |
| Actuation | 5 | 5 | 5 | |
| Units per actuation | 2.0 | 2.0 | 2.1 | |
| Particle size (μm) | 8.8 | 5.8 | 5.7 | |

*not determined/detected

TABLE XIV

| Stage No. | 0 | 1 | 2 | 3 |
|---|---|---|---|---|
| Volume (mL) | 10 | 10 | 10 | 10 |
| Mass (mg) | 0.79 | 0.81 | 0.78 | ** |
| Units | 20.7 | 21.0 | 20.1 | |
| Actuation | 5 | 5 | 5 | |
| Units per actuation | 4.15 | 4.18 | 4.01 | |
| Particle size (μm) | 9 | 5.8 | 4.7 | |

** not determined

Based on these tests, the particle size was determined to be about 7 μm, and stages 3–8 showed no einsulin deposition, indicating that most particles were larger than about 6 μm. This suggests that there would be no deep lung deposition formulation and that most of the formulation would be deposited in the buccal cavity.

What is claimed is:

1. A pressurized container containing a stable solubilized mixture of propellant which is liquid under pressure and an intermediate aerosol formulation which comprises a pharmaceutical agent, water, first ingredient, second ingredient and at least one third ingredient, wherein the first ingredient is selected from the group consisting of glycerin and polyglycerin and mixtures thereof in an amount of from 1–50 wt./wt. % of the intermediate formulation, the second ingredient is selected from the group consisting of phenol, methyl phenol and mixture's thereof in an amount of from 1–20 wt./wt. % of the intermediate formulation, each third ingredient is selected from the group consisting of alkali metal C8 to C22 alkyl sulphate, polidocanol C6 to C40 alkyl ethers, trihydroxy sodium oxo-cholanyl glycines, polyoxethylene sorbitan ethers, alkyl-aryl polyether alcohols, hyaluronic acidl and pharmaceutically suitable salts thereof, monoolein, triolein, lysine, polylysine, oleic acid, linoleic acid, linolenic acid, monooleates and laurates, glycolic acid, lactic acid, chenodeoxycholate, deoxycholate, chamomile extract, cucumber extract, borage oil and evening primrose oil and mixtures thereof, in an amount of from 1–50 wt./wt. % of the intermediate formulation, and wherein the total concentration of first, second and third ingredients is less than 90 wt.lwt. % of the intermediate formulation.

2. The container according to claim 1 wherein the alkali metal C8 to C22 alkyl sulphate is in a concentration of from 2 to 20 wt./wt. % of the intermediate formulation.

3. The container according to claim 2 wherein the alkali metal C8 to C22 alkyl sulphate is sodium lauryl sulphate.

4. The container according to claim 1 wherein the methyl phenol is m-cresol.

5. The container according to claim 1 wherein the polidocanol alkyl ether is a polidocanol 10 or 20 lauryl ether.

6. The container according to claim 1 wherein the polyoxyethylene ether is polyoxyethylene sorbitan 80 lauryl ether.

7. The container according to claim 1 wherein each third ingredient is present in a concentration of from about 1 to about 25 wt./wt. %.

8. The container according to claim 1 wherein the propellant is selected from the group consisting of tetrafluoroethane, tetrafluoropropane, dimethylfluoropropane, heptafluoropropane, dimethyl ether, n-butane and isobutane.

9. The container according to claim 8 wherein the weight ratio of pharmaceutical agent to propellant is from 5:95 to 25:75.

10. The container according to claim 1 wherein the pharmaceutical agent, water, first, second and third ingredients and propellant have been solubilized by a process comprising the steps of:
    a) dissolving the pharmaceutical agent in water and adjusting the pH to a level suitable for pharmaceutical use;
    b) mixing with the first ingredient in an amount of from 1–50 wt./wt. % of the intermediate formulation;
    c) then mixing with the second ingredient in an amount of from 1–20 wt./wt. % of the intermediate formulation;
    d) subsequently adding and mixing at least one third ingredient to form the intermediate formulation;
    e) charging the intermediate formulation to a pressurizable container and subsequently charging the container with the propellant.

11. A container according to claim 1 wherein the pharmaceutical agent is selected from the group consisting of insulin, heparin, low molecular weight heparin, hirulog, hirugen, buridine, interferons, interleukins, cytokins, mono and polyclonal antibodies, immunoglobins, chemotherapeutic agents, vaccines, glycoproteins, bacterial toxoids, hormones, calcitonins, insulin like growth factors (IGF), glucagon like peptides (GLP-1), antibiotics, thrombolytic compounds, platelet inhibitors, DNA, RNA, gene therapeutics and antisense oligonucleotides, opioids, narcotics, hypnotics, steroids, pain killers and non-steroidal anti-inflammatory drugs.

12. A container according to claim 11 wherein the pharmaceutical agent is insulin.

13. A process for making a stable aerosol pharmaceutical composition in which a propellant and an intermediate formulation, which comprises a pharmaceutical agent, water and first, second and third ingredients, has been solubilized by a process comprising the steps of:
    a) dissolving the pharmaceutical agent in water and adjusting the pH to a level suitable for pharmaceutical use;
    b) mixing with a first ingredient selected from the group consisting of glycerin, polyglycerin and mixtures thereof in an amount of from 1–50 wt./wt. % of the intermediate formulation;
    c) then mixing with a second ingredient selected from the group consisting of phenol, methyl phenol and mixtures thereof in an amount of from 1–20 wt./wt. % of the intermediate formulation;
    d) subsequently adding and mixing at least one third ingredient to form the intermediate formulation, said third ingredient being selected from the group consisting of alkali metal C8 to C22 alkyl sulphate, polidocanol C6 to C40 alkyl ethers, trihydroxy sodium oxo-cholanyl glycines, polyoxyethylene sorbitan ethers, alkyl-aryl polyether alcohols, hyaluronic acid and pharmaceutically suitable salts thereof, monoolein, triolein, lysine, polylysine, oleic acid, linoleic acid, linolenic acid, monooleates and laurates, glycolic acid, lactic acid, chenodeoxycholate, deoxycholate, chamomile extract, cucumber extract, borage oil and evening primrose oil, said third ingredient being present in an amount of from 1–50 wt./wt. % of the intermediate formulation, and wherein the total concentration of first, second and third ingredients are less than 90 wt.!wt. % of the intermediate formulation;

e) charging the intermediate formulation to a pressurizable container and subsequently charging the container with the propellant.

14. A process according to claim 13 wherein the alkali metal C8 to C22 alkyl sulphate is in a concentration of from 2 to 20 wt./wt. % of the intermediate formulation.

15. A process according to claim 14 wherein the alkali metal C8 to C22 alkyl sulphate is sodium lauryl sulphate.

16. A process according to claim 13 wherein the methyl phenol is m-cresol.

17. A process according to claim 13 wherein the polidocanol alkyl ether is a polidocanol 10 or 20 lauryl ether.

18. A process according to claim 13 wherein the polyoxyethylene ether is polyoxyethylene sorbitan 80 lauryl ether.

19. A process according to claim 13 wherein in step a) the pH is adjusted to between 6.0 and 9.0.

20. A process according to claim 13 wherein the propellant is selected from the group consisting of tetrafluoroethane, tetrafluoropropane, dimethylfluoropropane, heptafluoropropane, dimethyl ether, n-butane and isobutane.

21. A process according to claim 20 wherein the weight ratio of proteinic pharmaceutical agent to propellant is from 5:95 to 25:75.

22. A process according to claim 13 wherein step d) is accomplished with a high speed mixer or sonicator.

23. A process according to claim 13 wherein the pharmaceutical agent is selected from the group consisting of insulin, heparin, low molecular weight heparin, hirulog, hirugen, huridine, interferons, interleukins, cytokins, mono and polyclonal antibodies, immunoglobins, chemotherapeutic agents, vaccines, glycoproteins, bacterial toxoids, hormones, calcitonins, insulin like growth factors (IGF), glucagon like peptides (GLP-1), antibiotics, thrombolytic compounds, platelet inhibitors, DNA, RNA, gene therapeutics and antisense oligonucleotides, opioids, narcotics, hypnotics, steroids, pain killers and non-steroidal antiinflammnatory drugs.

24. A process according to claim 23 wherein the pharmaceutical agent is insulin.

25. A method for treatment of a medical condition by administering a pharmaceutical agent buccally or into lungs by spraying the pharmaceutical agent from a pressurized container containing a stable solubilized mixture of propellant which is liquid under pressure and an intermediate aerosol formulation which comprises the pharmaceutical agent, water, first ingredient, second ingredient and at least one third ingredient, wherein the first ingredient is selected from the group consisting of glycerin and polyglycerin and mixtures thereof in an amount of from 1–50 wt./wt. % of the intermediate formulation, the second ingredient is selected from the group consisting of phenol, methyl phenol and mixtures thereof in an amount of from 1–20 wt./wt. % of the intermediate formulation, each third ingredient is selected from the group consisting of alkali metal C8 to C22 alkyl sulphate, polidocanol C6 to C40 alkyl ethers, trihydroxy sodium oxo-cholanyl glycines, polyoxyethylene sorbitan ethers, alkyl-aryl polyether alcohols, hyaluronic acid and pharmaceutically suitable salts thereof, monoolein, triolein, lysine, polylysine, oleic acid, linoleic acid, linolenic acid, monooleates and laurates, glycolic acid, lactic acid, chenodeoxycholate, deoxycholate, chamomile extract, cucumber extract, borage oil and evening primrose oil and mixtures thereof, in an amount of from 1–50 wt./wt. % of the intermediate formulation, and wherein the total concentration of first, second and third ingredients is less than 90 wt./wt. % of the intermediate formulation.

26. A method according to claim 25 wherein the pharmaceutical agent is administered buccally.

27. A method according to claim 25 wherein the pharmaceutical agent is administered by spraying the formulation into the lungs.

* * * * *

UNITED STATES PATENT AND TRADEMARK OFFICE
CERTIFICATE OF CORRECTION

PATENT NO. : 6,315,984 B1
DATED : November 13, 2001
INVENTOR(S) : Pankaj Modi

It is certified that error appears in the above-identified patent and that said Letters Patent is hereby corrected as shown below:

Column 4,
Line 10, "ate" should read -- are --.

Column 5,
Line 65, "araben" should read -- paraben --.

Column 6,
Line 60, remove the "-" after "inhaler".

Column 8,
Line 2, "Adtemperature" should read -- temperature --.

Column 12,
Line 2, insert -- X -- after "and".

Column 13,
Line 61, "100 AL" should read -- 100 µL --.

Column 14,
Line 42, "einsulin" should read -- insulin --.
Line 57, "mixture's" should read -- mixtures --.
Line 63, "acidl" should read -- acid --.

Column 15,
Line 4, "wt.lwt." should read -- wt./wt. --.
Line 46, "buridine" should read -- huridine --.

UNITED STATES PATENT AND TRADEMARK OFFICE
CERTIFICATE OF CORRECTION

PATENT NO. : 6,315,984 B1
DATED : November 13, 2001
INVENTOR(S) : Pankaj Modi

It is certified that error appears in the above-identified patent and that said Letters Patent is hereby corrected as shown below:

<u>Column 16,</u>
Line 23, "wt.!wt." should read -- wt./wt. --.

Signed and Sealed this

Fourth Day of June, 2002

Attest:

JAMES E. ROGAN
*Attesting Officer*  *Director of the United States Patent and Trademark Office*